(12) United States Patent
Holmes et al.

(10) Patent No.: US 12,059,263 B2
(45) Date of Patent: Aug. 13, 2024

(54) LIDAR IMPLANTABLE BIOSENSOR FOR IMAGING BIOLOGICAL TISSUE

(71) Applicant: International Business Machines Corporation, Armonk, NY (US)

(72) Inventors: Steven J. Holmes, Ossining, NY (US); Devendra K. Sadana, Pleasantville, NY (US); Stephen W. Bedell, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 18/359,363

(22) Filed: Jul. 26, 2023

(65) Prior Publication Data

US 2023/0363694 A1    Nov. 16, 2023

Related U.S. Application Data

(62) Division of application No. 16/447,324, filed on Jun. 20, 2019, now Pat. No. 11,864,906.

(51) Int. Cl.
*A61B 5/00*    (2006.01)

(52) U.S. Cl.
CPC .......... *A61B 5/4064* (2013.01); *A61B 5/0031* (2013.01); *A61B 5/0084* (2013.01); *A61B 5/742* (2013.01); *A61B 2562/0233* (2013.01); *A61B 2562/046* (2013.01)

(58) Field of Classification Search
CPC .................................................. A61B 5/4064
See application file for complete search history.

(56) References Cited

U.S. PATENT DOCUMENTS

| | | | |
|---|---|---|---|
| 5,833,603 A | * | 11/1998 | Kovacs ................... G01J 3/02 |
| | | | 600/109 |
| 5,853,370 A | | 12/1998 | Chance et al. |
| 6,125,290 A | | 9/2000 | Miesel |

(Continued)

FOREIGN PATENT DOCUMENTS

| | | |
|---|---|---|
| CN | 101947115 A | 1/2011 |
| CN | 105307559 B | 2/2016 |

(Continued)

OTHER PUBLICATIONS

C.-J. Chang et al., "Noninvasive Imaging Analysis of Biological Tissue Associated with Laser Thermal Injury," Biomedical Journal, Apr. 2017, pp. 106-112, vol. 40, No. 2.

(Continued)

*Primary Examiner* — Joseph M Santos Rodriguez
(74) *Attorney, Agent, or Firm* — Anthony Mauricio Pallone; Ryan, Mason & Lewis, LLP (57) ABSTRACT

A method includes implanting an implantable biosensor within a subject where the implantable biosensor has an array of light sources and an array of light detectors, activating the array of light sources to direct light signals at a targeted tissue site in the subject, capturing, with the light detectors, the light signals reflected off the targeted site, calculating a roundtrip propagation time for each of the light signals and comparing the roundtrip propagation time for each of the light signals against previous calculated respective roundtrip propagation times to determine an occurrence of a change in the targeted tissue site.

20 Claims, 8 Drawing Sheets

(56) References Cited

U.S. PATENT DOCUMENTS

| | | |
|---|---|---|
| 7,729,773 B2 | 6/2010 | Sloan |
| 10,219,729 B2 | 3/2019 | Kintz et al. |
| 2006/0217793 A1 | 9/2006 | Costello |
| 2007/0027371 A1 | 2/2007 | Benaron et al. |
| 2007/0100398 A1 | 5/2007 | Sloan |
| 2008/0123800 A1 | 5/2008 | Joshi et al. |
| 2008/0133551 A1 | 6/2008 | Wensley et al. |
| 2010/0317939 A1 | 12/2010 | Kuhn et al. |
| 2011/0125208 A1 | 5/2011 | Karst et al. |
| 2014/0094674 A1 | 4/2014 | Nurmikko et al. |
| 2014/0107440 A1 | 4/2014 | Kuhn et al. |
| 2015/0119725 A1 | 4/2015 | Martin et al. |
| 2016/0161600 A1 | 6/2016 | Eldada et al. |
| 2017/0061034 A1 | 3/2017 | Ritchey et al. |
| 2017/0105622 A1 | 4/2017 | Boesen et al. |
| 2017/0299697 A1 | 10/2017 | Swanson |
| 2018/0014113 A1 | 1/2018 | Boesen |
| 2018/0065017 A1 | 3/2018 | Murdock et al. |
| 2018/0070830 A1 | 3/2018 | Sutin et al. |
| 2018/0153410 A1 | 6/2018 | Islam |
| 2018/0306925 A1 | 10/2018 | Hosseini et al. |
| 2022/0047167 A1 | 2/2022 | Islam |

FOREIGN PATENT DOCUMENTS

| | | |
|---|---|---|
| JP | 2008228866 A | 10/2008 |
| JP | 2017144225 A | 8/2017 |
| WO | 2008133551 A1 | 11/2008 |
| WO | 2020254944 A1 | 12/2020 |

OTHER PUBLICATIONS

S. I. Al-Juboori et al., "Light Scattering Properties Vary Across Different Regions of the Adult Mouse Brain," PLoS One, Jul. 9, 2013, 9 pages, vol. 8, No. 7.

J. F. Holmes et al., "Adapting Atmospheric LIDAR Techniques to Imaging Biological Tissue," Proceedings of SPIE, Laser-Tissue Interaction XI: Photochemical, Photothermal, and Photomechanical, Jun. 13, 2000, pp. 454-459, vol. 3914.

G. Greneker, "Radar Technology for Acquiring Biological Signals," The Journal of Credibility Assessment and Witness Psychology, 2006, pp. 127-134, vol. 7, No. 2.

C. V. Poulton et al., "Coherent Solid-State LIDAR with Silicon Photonic Optical Phased Arrays," Optics Letters, Oct. 15, 2017, pp. 4091-4094, vol. 42, No. 20.

P. Protiva et al., "Sub-Nanosecond Pulse Generator for Through-the-Wall Radar Application," European Microwave Conference (EuMC), Sep. 29-Oct. 1, 2009, 4 pages.

J. M. Sill et al., "Tissue Sensing Adaptive Radar for Breast Cancer Detection—Experimental Investigation of Simple Tumor Models," IEEE Transactions on Microwave Theory and Techniques, Nov. 2005, pp. 3312-3319, vol. 53, No. 11.

Y. Ning et al., "Reproducible Sensing of Individual Biological Cells by Broadband Microwave Signals," IEEE Benjamin Franklin Symposium on Microwave and Antenna Sub-Systems for Radar, Telecommunications, and Biomedical Applications (BenMAS), Sep. 26, 2014, 3 pages.

J. Lin et al., "Review-Semiconductor Integrated Radar for Sensing Applications," ECS Journal of Solid State Science and Technology, Apr. 18, 2018, pp. 3126-3142, vol. 7, No. 7.

List of IBM Patents or Patent Applications Treated as Related.

United Kingdom IPO Examination Report under Section 18(3) for Application No. GB2200313.1, Jan. 9, 2023, 3 pages.

International Search Report and Written Opinion of PCT/IB2020/055581, dated Jun. 17, 2020, 10 pages.

Response to United Kingdom IPO Examination Report under Section 18(3) for Application No. GB2200313.1, Feb. 21, 2023, 2 pages.

German Patent Application No. 112020001916.0, Examination notice , Oct. 4, 2023, 12 pages.

Japanese Patent Application No. 2021-574751, Notice of Reasons for Refusal, Jul. 18, 2023, 6 pages.

* cited by examiner

LIDAR IMPLANTABLE BIOSENSOR FOR IMAGING BIOLOGICAL TISSUE

BACKGROUND

Illustrative embodiments generally relate to sensing of biological tissues, and, more particularly, relate to an implantable biosensor using light detection and ranging (LIDAR) techniques for detecting changes in neural tissue at the cellular level.

Existing sensing techniques for biological tissues, especially neural tissue, cannot provide information concerning the details of cellular structure for a particular cell, or how the cellular structure changes with time. Current methods of sensing neural tissue provide indirect evidence of cell or tissue structure, for example, the release of neurotransmitters or ions can be measured, but this does not provide a direct view of the cellular structure or provide data concerning changes in cellular structure. The ability to monitor changes in neural tissue, particularly, brain cells, may provide a greater understanding in brain functioning, adaptability, diagnosis and progression of neural diseases states. In addition, information regarding changes in brain cell structure upon exposure to various stimuli including electrical charges, pharmaceuticals, hormones, etc. may provide avenues into potential new treatments for various brain diseases including Alzheimer's disease, dementia, cancer, epilepsy and other seizure disorders, mental illness. Parkinson's disease, etc.

SUMMARY

In accordance with one illustrative embodiment, a method comprises implanting an implantable biosensor within a subject where the implantable biosensor comprises an array of light sources and an array of light detectors, activating the array of light sources to direct light signals at a targeted tissue site in the subject, capturing, with the light detectors, the light signals reflected off the targeted site, calculating a roundtrip propagation time for each of the light signals and comparing the roundtrip propagation time for each of the light signals against previous calculated respective roundtrip propagation times to determine an occurrence of a change in the targeted tissue site.

In accordance with another illustrative embodiment, a system comprises an implantable biosensor configured for implantation within a subject where the implantable biosensor comprises an array of light sources and an array of light detectors. The array of light sources is configured to direct tight signals at a targeted tissue site in the subject. The light detectors are configured to capture the light signals reflected off the targeted site. The apparatus further includes a processor coupled with memory and configured to calculate a roundtrip propagation time for each of the light signals, and compare the roundtrip propagation time for each of the light signals against previous calculated respective roundtrip propagation times to determine an occurrence of a change in the targeted tissue site.

In accordance with another illustrative embodiment, a computer program product for detecting changes in structure of one or more brain cells, comprises a non-transitory computer readable medium encoded with computer-executable code. The code is configured to enable the execution of calculating roundtrip propagation time of light signals emitted by an implantable biosensor implanted within the brain, and comparing the roundtrip propagation times for each of the light signals against previously calculated respective roundtrip propagation times to determine an occurrence of a change in structure of one or more brain cells.

Other embodiments will be described in the following detailed description of embodiments, which is to be read in conjunction with the accompanying figures.

DETAILED DESCRIPTION

Illustrative embodiments are directed to a neural biosensor implantable within the brain of a subject and utilized to gather data concerning cell structure and to monitor potential changes in cell structure as a function of time, for example, age, and/or when subjected to various stimuli, when in a diseased state, etc. The implantable biosensor incorporates light detection and ranging (LIDAR) technology appropriately scaled to analyze cell tissue via detectors and/or optics incorporated with the biosensor.

In general, light detection and ranging (LIDAR) techniques have gained significant interest due to, amongst other reasons, its ability to provide high resolution of various objects. Historically, LIDAR has seen extensive use in autonomous vehicles, robotics, aerial mapping, and atmospheric measurements, and, more recently, has found application in 3-D imaging. A typical LIDAR sensor is a light detection and ranging sensor incorporating an optical sensing module that can calculate the distance to a target, by irradiating the target with pulsed or modulated laser light, and measuring the emission time and return time of the light to and from a receiver in the module. i.e., the total roundtrip propagation time of a light signal. In LIDAR technology, the roundtrip propagation time is also referred to as "time of flight" (hereinafter, "ToF"). The ToF of the lasers and wavelengths are then used to create digital 3-D representations of the target.

Most recently. LIDAR has been used as an imaging vehicle through the use of arrays of high-speed detectors and modulation sensitive detectors, which may be built on single biosensors using semiconductor fabrication techniques. In these devices, each pixel performs some local processing such as demodulation or gating at high speed, and down converting the signals to video rate so that the array can be read like a camera. Using this technique many thousands of pixels/channels may be acquired simultaneously providing a mapping or image of the object.

Accordingly, illustrative embodiments are directed to implementing LIDAR technology on a semiconductor device or biosensor which is specifically dimensioned (scaled down) for implantation within the subject's body (e.g., humans, animals, etc.), for example, in the brain of the subject. Although the following description will focus on use of the implantable biosensor in the brain, it is appreciated that the implantable biosensor may have other implantable applications including the heart, peripheral nervous system, stomach and other organs of the body.

It is to be understood that the embodiments discussed herein are not limited to the particular materials, features, and processing steps shown and described herein. In particular, it is to be emphasized that the descriptions provided herein are not intended to encompass all of the details that may be required to form an implantable biosensor. Rather, certain features including processing steps that are commonly used are purposefully not described herein for economy of description.

Moreover, the same or similar reference numbers are used throughout the drawings to denote the same or similar features, elements, or structures, and thus, a detailed explanation of the same or similar features, elements, or structures will not be repeated for each of the drawings. The terms "about" or "substantially" as used herein with regard to thicknesses, widths, percentages, ranges, etc., are meant to denote being close or approximate to, but not exactly. For example, the term "about" or "substantially" as used herein implies that a small margin of error is present. Further, the terms "vertical" or "vertical direction" or "vertical height" as used herein denote a Z-direction of the Cartesian coordinates shown in the drawings, and the terms "horizontal," or "horizontal direction," or "lateral direction" as used herein denote an X-direction and/or Y-direction of the Cartesian coordinates shown in the drawings.

Additionally, the term "illustrative" is used herein to mean "serving as an example, instance or illustration." Any embodiment or design described herein is intended to be "illustrative" and is not necessarily to be construed as preferred or advantageous over other embodiments or designs.

Figure 1:
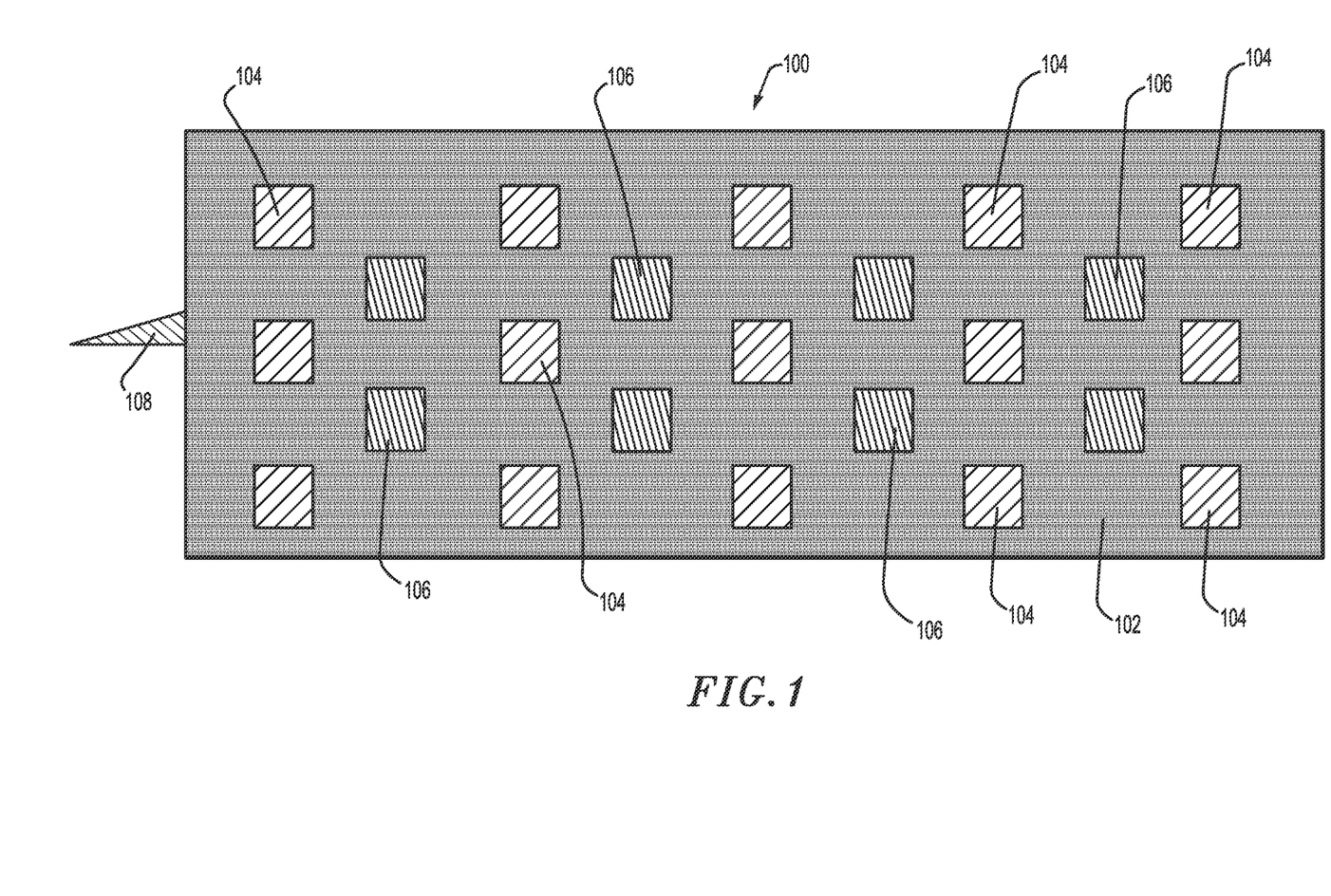
FIG. 1 is a schematic top plan view of the implantable biosensor, according to one or more illustrative embodiments.

An illustrative embodiment of an implantable biosensor will be described below with initial reference to FIG. 1. Note that the implantable biosensor described herein can also be considered to be a semiconductor device and/or an integrated circuit, or some part thereof. FIG. 1 is a top plan view of the implantable biosensor 100 in accordance with the principles of the present disclosure. The implantable biosensor device 100 includes a substrate 102, for example, a semiconductor wafer, which houses the various semiconductor devices and components (not shown) that are formed in or on the active surface of the wafer to provide integrated circuitry for a target application as a result of layer processing. For example, while the substrate 102 is schematically depicted for ease of illustration, it is to be understood that the substrate 102 comprises multiple layers including a semiconductor wafer substrate layer. The semiconductor wafer substrate comprises one of different types of semiconductor wafer substrate structures and materials. For example, in one embodiment, the semiconductor wafer substrate can be a bulk semiconductor wafer substrate that is formed of silicon (Si) or germanium (Ge), or other types of semiconductor substrate materials which are commonly used in bulk semiconductor fabrication processes such as a silicon-germanium alloy, compound semiconductor materials (e.g., II-V), etc. In another embodiment, the semiconductor wafer substrate may comprise an SOI (silicon-on-insulator) substrate, GeOI (germanium-on-insulator) substrate, or other types of semiconductor-on-insulator substrates which comprise an insulating layer (e.g., oxide layer) disposed between a base substrate layer (e.g., silicon substrate) and the active semiconductor layer (e.g., Si, Ge, etc.) having circuit components.

The substrate includes various semiconductor devices and components that are formed in or on an active surface of the semiconductor wafer substrate to provide integrated circuitry for a target application. For example, the substrate may include field-effect transistor (FET) devices (such as FinFET devices, vertical FET devices, planar FET devices, etc.), bipolar transistors, diodes, capacitors, inductors, resistors, isolation devices, etc., which are formed in or on the active surface of the semiconductor wafer substrate. Moreover, the substrate 102 may include components that are part of FEOL (front-end-of-line)/MOL (middle-of-line) layer processing.

The implantable biosensor 100 also includes a light source for generating light signals and directing light signals at the cell structure. The light source includes an array of low power light emitting diodes (LED) 104 positioned in spaced relation relative to the substrate 102. In other illustrative embodiments, the light source may include one or more low power lasers. The implantable biosensor 100 further includes an array of light detectors 106 also positioned in spaced relation relative to the substrate 102. The light detectors 106 are adapted to detect the light signals reflected off the cell structure, which will provide data to create an image of the cell structure based upon the ToF of the light signals, as will be discussed hereinbelow. Optionally, the light detectors may comprise a pixelated imaging array having a plurality of photo-sensing pixels arranged or disposed or established on the substrate 102. For example, the light detectors 106 may comprise a complementary-metal-oxide-semiconductor (CMOS) or a charge-coupled device (CCD) imaging sensor or device or the like, i.e., the array of light detectors 106 can be a CCD array or a light detector array.

In one or more embodiments, the LEDS 104 and the light detectors 106 are fabricated using materials that are compatible with a biological environment, such as a body, as well as compatible with processing needs of other integrated devices. In illustrative embodiments, the LEDS 104 and the light detectors 106 are fabricated using a gallium nitride (GaN) material. Various known semiconductor fabrication techniques for fabricating the LEDS 104 and the light detectors 106 on the substrate 102 may be utilized.

The implantable biosensor 100 may include structure which securely fixes the substrate 102 of the implantable biosensor 100 within the brain of the subject. Such structure may include a penetrating member such as a pin, fork or the like attached to the substrate 102 as schematically shown as reference numeral 108 in FIG. 1. Other methodologies for securing the implantable biosensor 100 are also envisioned, including with the use of a bio-adhesive material.

In general, the implantable biosensor 100 once implanted in the brain of the subject is actuated whereby the LEDS 104 emit light signals at a pulse rate in the range of milliseconds. Alternatively, depending on the potential rate of change expected of the brain cells, the pulse rate may be seconds, minutes or even hours for some applications. The wavelength may range from about 400 (nanometers) nm to 1200 nm, or even greater than 1200 nm. Wavelengths below 400 nm potentially may result in the absorption of too much light by the brain cells. Longer wavelengths may result in reduced resolution, buy even resolution at the micron range may be useful for many applications. The light signals from the LEDS 104 reflect off the targeted brain cell, and are captured by the light detectors 106. Any changes from a previously determined baseline ToF of one or more of the captured light signals originally emanating from each individual LED source or sources 104 is indicative of a change in structure of the targeted brain cell.

Figure 2:
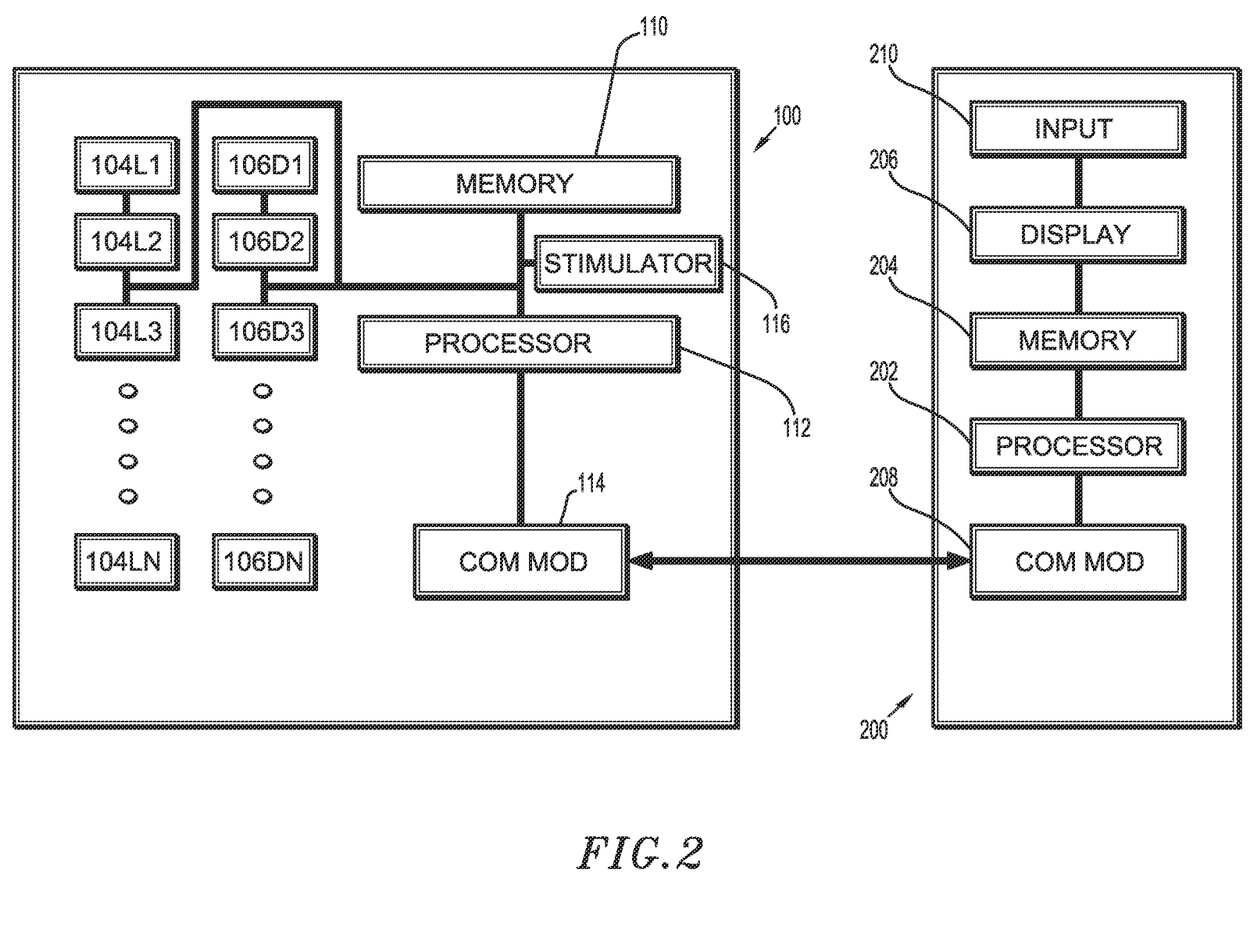
FIG. 2 is a block diagram illustrating the framework of the implantable biosensor, according to one or more illustrative embodiments.

Referring now to FIG. 2, there is illustrated the framework of a comprehensive system of the implantable biosensor 100 for detecting changes in cell structure(s) of the brain. In one illustrative embodiment, the implantable biosensor 100 is shown including a plurality of LEDS 104L1, 104L2, 104L3, . . . 104LN and light detectors 106D1, 106D2, 106D3, . . . 106DN. The implantable biosensor 100 further includes a memory 110 with software or logic programmed to perform the various functions associated with transmission and reception of light, one or more microprocessors 112 coupled to the memory 110 and a communication module 114 to establish communication with a remote device 200. In some illustrative embodiments, the logic provides data representative of ToF for each light signal emitted by a particular LED 104L1, 104L2, 104L3, . . . 104LN for further manipulation by the remote device 200. In other illustrative embodiments, the logic may be capable of forming images of the cell structure based on the ToF data for each emission of pulsed light. The implantable biosensor 100 may further include a stimulator 116 to impart, for example, an electric charge, vibrations etc. to the brain cells to intentionally cause changes in the cell structure. Alternatively, or additionally, the stimulator 116 may be used to change functioning of the brain cells, including altering the release of chemicals such as dopamine, oxytocin, serotonin, and/or endorphins.

The remote device 200 may be a server in communication with the implantable biosensor either directly or indirectly. The server may include a processor 202 with memory 204 and associated logic capable of performing additional calculations on the data received from the implantable biosensor, and a visual display 206 to provide visualization of one or more brain cells to track structural changes of the cell(s). The server further includes a communication module ("COM MOD") 208 to communicate via wired or wireless transmission with the communication module 114 of the implantable biosensor.

Figure 3:
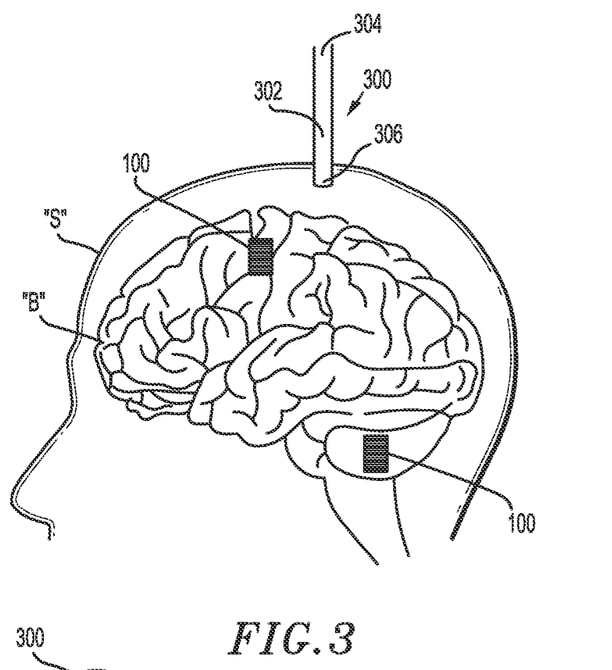
FIG. 3 is a view illustrating the implantable biosensor implanted within the brain of a subject, according to one or more illustrative embodiments.

FIG. 3 illustrates the implantable biosensor 100 implanted within the brain "B" of a subject. Various methodologies for implanting the implantable biosensor 100 are contemplated including, for example, open surgery. In one illustrative embodiment, the implantable biosensor 100 is implanted via an access device 300. The access device 300 is configured to provide access to the brain "B" of the subject to facilitate the implantation of the implantable biosensor 100 on, or at least partially within, the brain "B." The access device 300 can be prepared with growth enhancing material, for example, stem cell material, such that, once implanted, the device 300 can bind to a bone of the skull "S" or the skin covering the skull "S". In some embodiments, the access device 300 is the remote device 200 discussed in connection with FIG. 2, and thus can be provided with one or more connectors, a processor, a memory, and one or more communication components, for example, wireless transmission capabilities to facilitate the reception and transmission of data captured by the implantable biosensor 100 as discussed hereinabove. In illustrative embodiments, the access device 300 may be in communication with the remote device 200 to transmit data from the implantable biosensor 100 to the remote device 200.

The access device 300 comprises a cylindrical surface 302 enclosed by an external end 304 (e.g., top side) and an internal end 306 (e.g., bottom side). In some embodiments, the external end 304 includes or defines an external connection (e.g., a first connector component) that can be used to make direct or non-direct (e.g., magnetic or wireless) connection to external devices (e.g., diagnostic devices) such as the remote device 200. In some embodiments, the internal end 306 also includes or defines an internal connection. The connection of the external end 304 may be configured to provide an electrical interface (either wired or via wireless transmission) with the external devices such as the remote device 200 and components inside the access device 300.

To implant the access device 300, a portion of the access device 300 is prepared using any suitable device implanting technique such that the access device 300 can be bound to the bone of the skull "S." For example, growth enhancing material (e.g., bone tissues) collected from the bone of the subject can be applied and grown on a portion of the access device 300 prior to implantation. An aperture, the size of the access device 300 can be formed in the bone of the skull "S". Thereafter, the cranial access device 300 can be implanted in the aperture. After implantation, the bone tissues become integrated with the existing bone and creates a permanent integration of the access device 300 with the existing bone. In some embodiments, the clinicians may be communicating with the implantable biosensor 100 implanted in or on the brain. Binding the access device 300 to the bone of the skull "S" addresses the problem of limited or no access to cranial regions without having to perform medical procedures to retrieve data or provide treatment, resulting in solutions that can allow quicker access to devices implanted in the cranial regions and allow using simple techniques to treat the subject or retrieve diagnostic information.

In some embodiments, the access device 300 can be communicatively coupled to the implantable biosensor 100 using wireless technology. The wireless technology can be incorporated in the access device 300. The wireless technology can be used to transmit electrical pulses or establish communication between the access device 300 and the implantable biosensor 100. It is envisioned that the access device 300 can actuate functions of the implantable biosensor 100. For example, the implantable biosensor 100 can wirelessly receive commands to generate vibrations, electrical pulses or transmit the diagnosis data.

Figure 4:
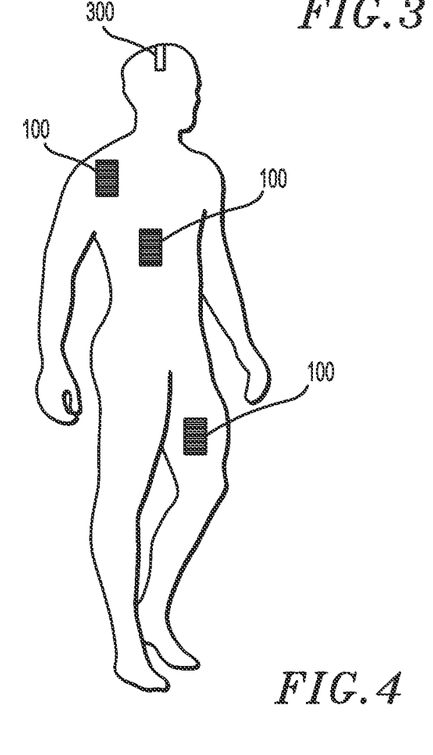
FIG. 4 is a view illustrating the implantable biosensor implanted within other regions of the body of the subject, according to one or more illustrative embodiments.

FIG. 4 is a view of the implantable sensor 100 implanted in other regions of the body. Such regions include but are not limited to, the peripheral nervous system, the abdomen, spinal tissue etc., and can be utilized in the manner to be discussed to detect changes in cell tissue in these regions.

Figure 5:
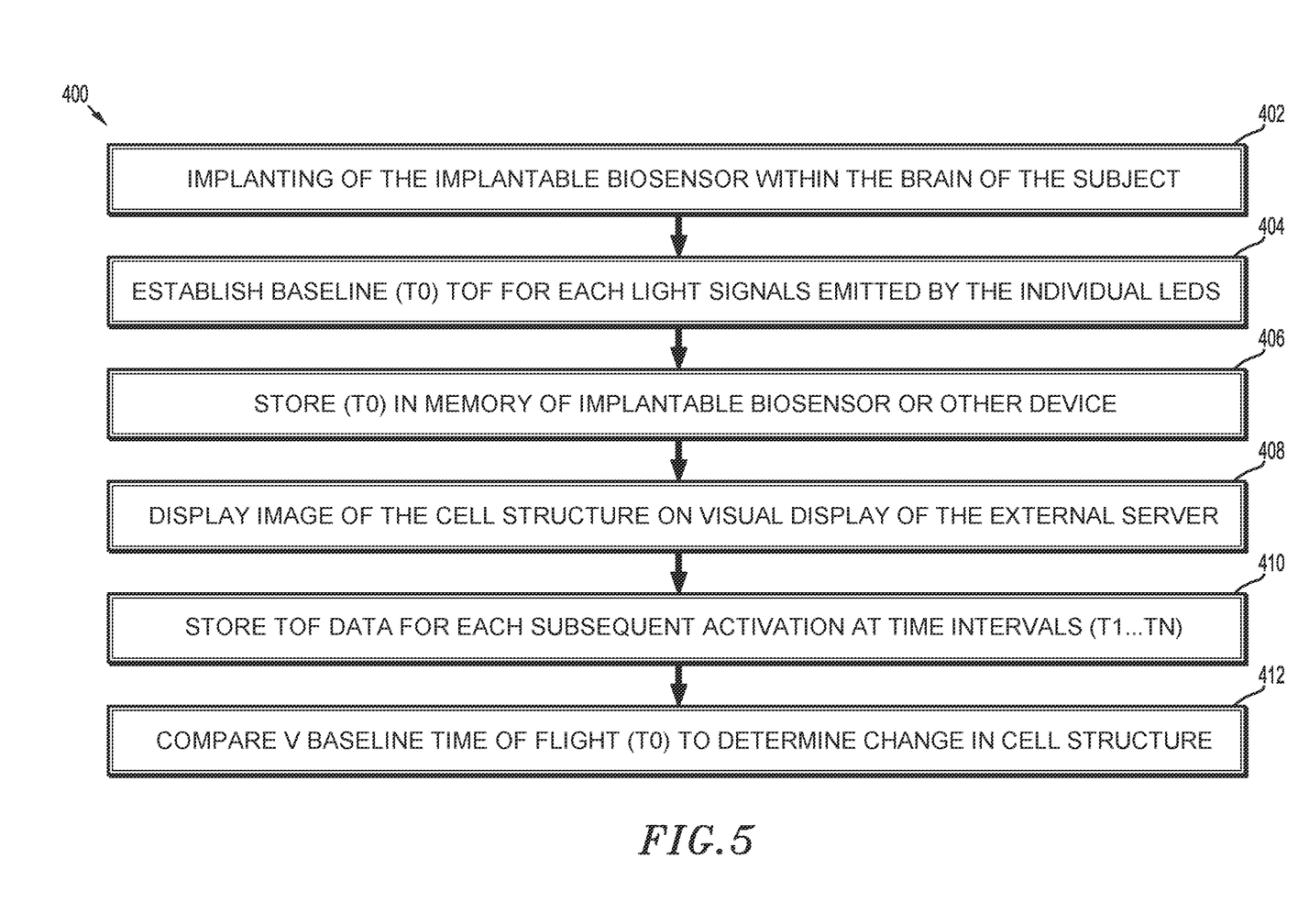
FIG. 5 is a flow chart depicting an illustrative method of use of the implantable biosensor to detect changes in cell structure, according to one or more illustrative embodiments.

FIG. 5 is a flow diagram of one illustrative use of the implantable biosensor 100. It is appreciated that the procedure is not limited to the steps set forth in FIG. 5. For example, more or less steps may be involved, and the steps may be combined or performed in a different sequence. The methodology 400 initially begins with implanting of the implantable biosensor 100 within the brain of the subject. (STEP 402). As discussed, the implantable biosensor 100 may be implanted via an open surgical approach or implanted with the use of the access device 300. In one illustrative embodiment, the access device 300 is introduced through the skull "S" of the subject providing access to the underlying targeted cell structures. The implantable biosensor 100 is introduced through the access device 300 and implanted at the targeted cell structure. Thereafter, the implantable biosensor 100 may be secured at the targeted site with the use of the penetrating member 108.

The procedure is continued by establishing a baseline of the structure of the cell by activating the LEDS 104 and the light detectors 106 to establish a baseline ToF (TO) for each of the light signals emitted by the individual LEDS 104. (STEP 404). The data concerning the ToF is stored in the memory of the implantable biosensor 100, the memory 204 of the remote device 200 via wireless transmission or the memory of the access device 300. (STEP 406). An image optionally may be provided of the cell structure on, for example, the visual display of the external server. (STEP 408). Thereafter, the ToF data for each subsequent activation of the individual LEDS 104 and light detectors 106, for example, at time intervals (T1 . . . TN) of the implantable biosensor 100, is captured and recorded in memory. (STEP 410). The ToF data and or associated images therewith are compared against the image or data of the baseline ToF (TO) to determine if any changes have occurred in the data which may be indicative of a change in the cell structure. (STEP 412). The process may be periodically continued to monitor the status of the cell structure(s).

Figure 6:
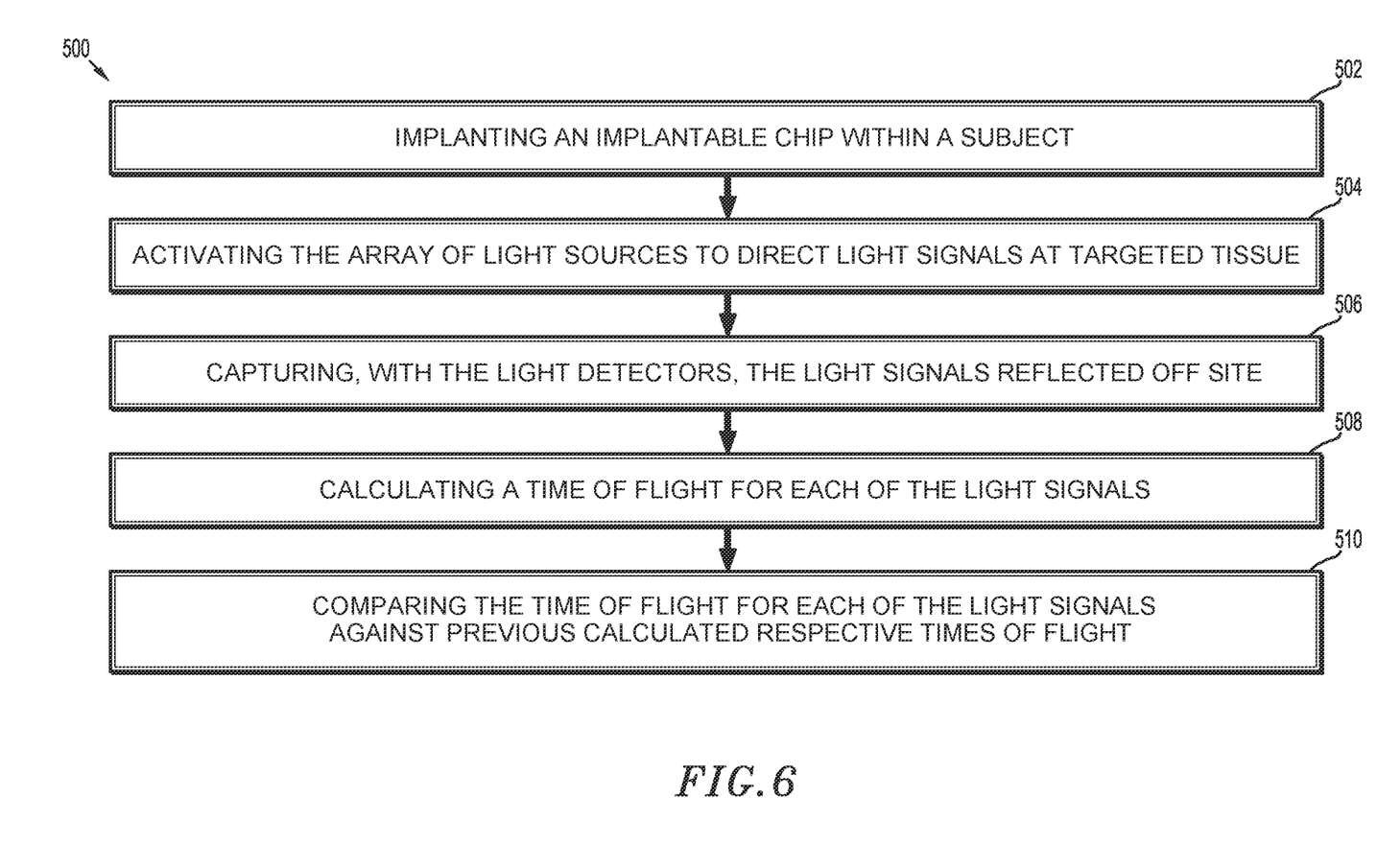
FIG. 6 is a flow chart depicting another illustrative method of use of the implantable biosensor, according to one or more illustrative embodiments.

FIG. 6 is another flow chart illustrating another exemplative use of the implantable biosensor 100. In accordance with the illustrative methodology 500 depicted in FIG. 6, the method 500 may comprise implanting an implantable biosensor 100 within a subject. (STEP 502). The implantable biosensor comprises an array of light sources 104 and an array of light detectors 106. The array of light sources, for example, in the form of LEDS 104, are activated to direct light signals at a targeted tissue site in the subject. (STEP 504). The light signals reflect off the targeted tissue, for example, one or more brain cells. The reflected light signals are captured by the light detectors 106. (STEP 506). A ToF for each of the individual light signals is calculated, (STEP 508). The ToF for each of the light signals is compared against previous calculated respective ToFs to determine an occurrence of a change in the targeted tissue site. (STEP 510).

Illustrative embodiments include a system, a method, and/or a computer program product at any possible technical detail level of integration. The computer program product may include a computer readable storage medium (or media) having computer readable program instructions thereon for causing a processor to carry out aspects of illustrative embodiments herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of illustrative embodiments described herein may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the illustrative embodiments described herein.

Aspects of the illustrative embodiments are described herein with reference to flowchart illustrations and/or block diagrams of methods, apparatus (systems), and computer program products according to the illustrative embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various illustrative embodiments described herein. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 7:
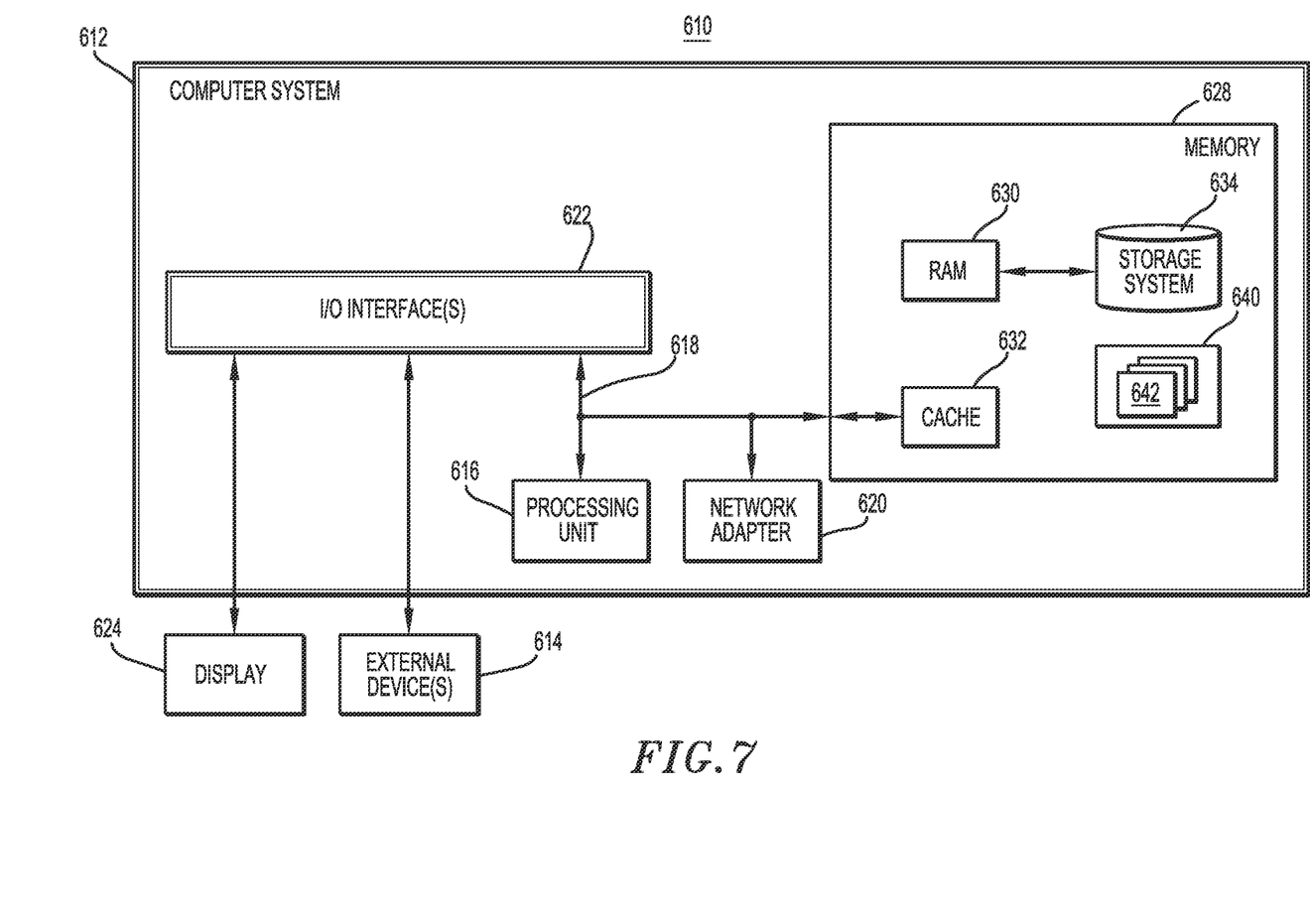
FIG. 7 illustrates a computer system in accordance with which one or more components/steps or techniques may be implemented, according to one or more illustrative embodiments.

One or more embodiments can make use of software running on a general-purpose computer or workstation. With reference to FIG. 7, in a computing node 610 there is a computer system/server 612, which is operational with numerous other general purposes or special purpose computing system environments or configurations. Examples of well-known computing systems, environments, and/or configurations that may be suitable for use with computer system/server 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, mobile and wearable devices, and distributed cloud computing environments that include any of the above systems or devices, and the like.

Computer system/server 612 may be described in the general context of computer system executable instructions, such as program modules, being executed by a computer system. Generally, program modules may include routines, programs, objects, components, logic, data structures, and so on that perform particular tasks or implement particular abstract data types. Computer system/server 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 612 in computing node 610 is shown in the form of a general-purpose computing device. The components of computer system/server 612 may include, but are not limited to, one or more processors or processing units 616, a system memory 628, and a bus 618 that couples various system components including system memory 628 to processor 616.

The bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 612 typically includes a variety of computer system readable media. Such media may be any available media that is accessible by computer system/server 612, and it includes both volatile and non-volatile media, removable and non-removable media.

The system memory 628 can include computer system readable media in the form of volatile memory, such as random-access memory (RAM) 630 and/or cache memory 632. The computer system/server 612 may further include other removable/non-removable, volatile/nonvolatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 618 by one or more data media interfaces. As depicted and described herein, the memory 628 may include at least one program product having a set (e.g., at least one) of program modules that are configured to carry out the functions of embodiments of illustrative embodiments herein. A program/utility 640, having a set (at least one) of program modules 642, may be stored in memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the illustrative embodiments as described herein.

Computer system/server 612 may also communicate with one or more external devices 614 such as a keyboard, a pointing device, a display 624, etc., one or more devices that enable a user to interact with computer system/server 612, and/or any devices (e.g., network card, modem, etc.) that enable computer system/server 612 to communicate with one or more other computing devices. Such communication can occur via I/O interfaces 622. Still yet, computer system/server 612 can communicate with one or more networks such as a LAN, a general WAN, and/or a public network (e.g., the Internet) via network adapter 620. As depicted, network adapter 620 communicates with the other components of computer system/server 612 via bus 618. It should be understood that although not shown, other hardware and/or software components could be used in conjunction with computer system/server 612. Examples include, but are not limited to, microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, illustrative embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. Them is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using program code languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
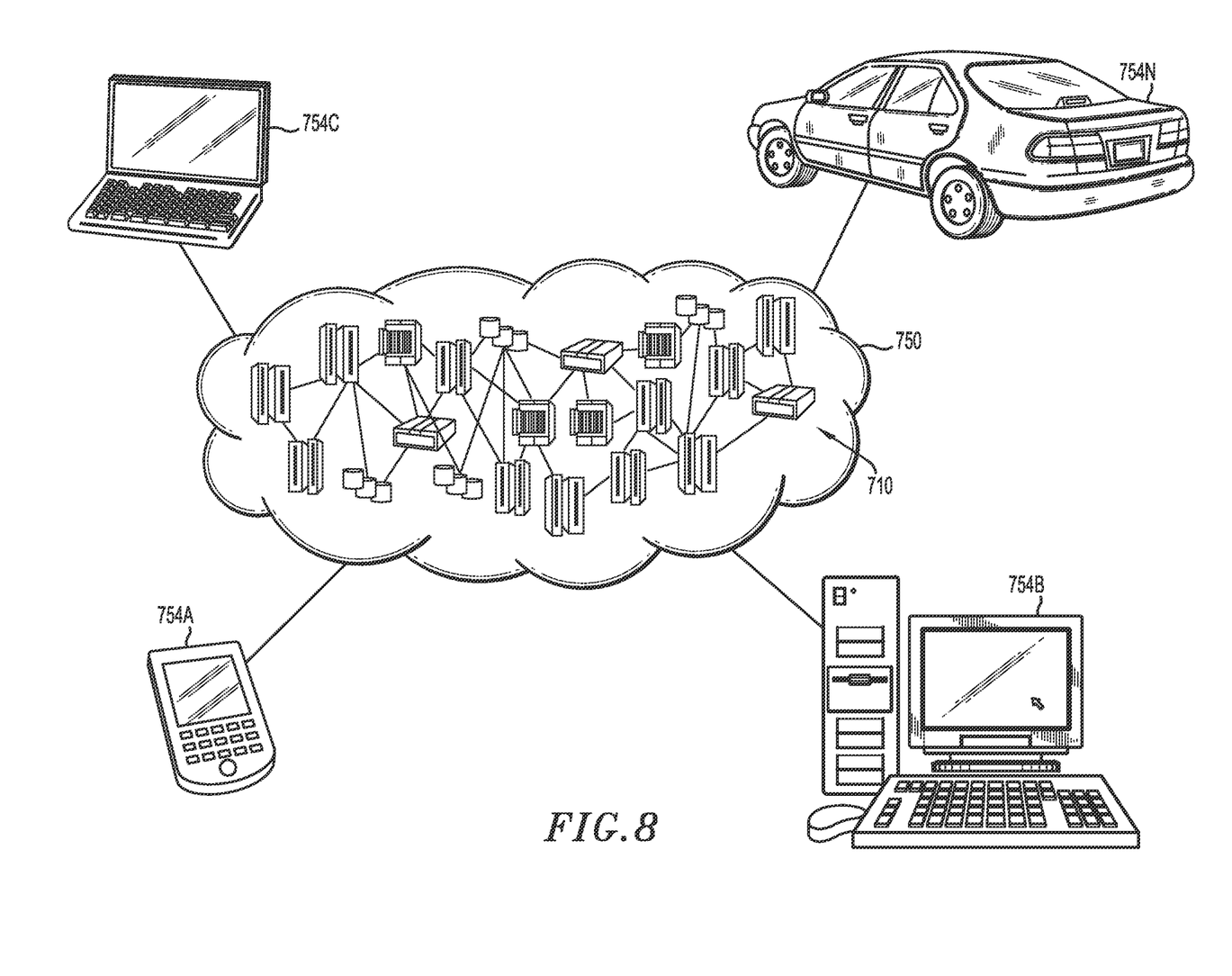
FIG. 8 illustrates a cloud computing environment according to one or more illustrative embodiments.

Referring now to FIG. 8, illustrative cloud computing environment 750 is depicted. As shown, cloud computing environment 750 includes one or more cloud computing nodes 710 with which local computing devices used by cloud consumers, such as, for example, personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private. Community. Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 8 are intended to be illustrative only and that computing nodes 710 and cloud computing environment 750 can communicate with any type of computerized device over any type of network and/or network addressable connection (e.g., using a web browser).

Figure 9:
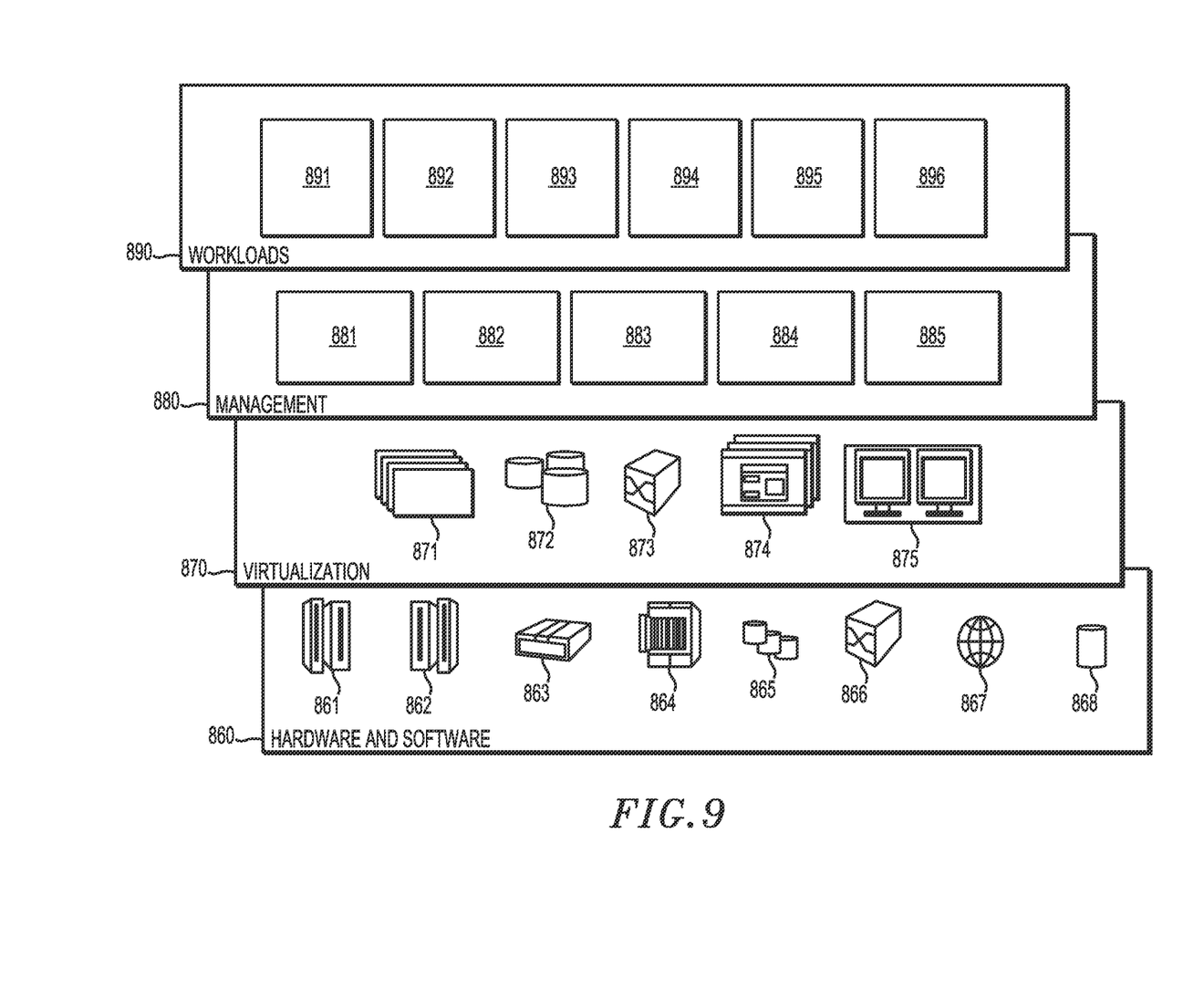
FIG. 9 illustrates abstraction model layers according to one or more illustrative embodiments.

Referring now to FIG. 9, a set of functional abstraction layers provided by cloud computing environment 750 (FIG. 8) is shown. It should be understood in advance that the components, layers, and functions shown in FIG. 9 are intended to be illustrative only and embodiments are not limited thereto. As depicted, the following layers and corresponding functions are provided:

Hardware and software layer 860 include hardware and software components. Examples of hardware components include: mainframes 861; RISC (Reduced Instruction Set Computer) architecture-based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and pricing 882 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from the workload layer 890 include data analytics processing 891, activating the implantable biosensor 892, establishing a baseline ToF for one or more cell structures 893, calculating subsequent ToFs for the one or more cell structures 894, comparing the subsequent ToFs against the baseline ToF 895 and making a determination of a change in cell structure 896 using the methodologies and techniques described herein.

The descriptions of the various illustrative embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   an implantable biosensor configured for implantation within a subject, the implantable biosensor comprising an array of light sources and an array of light detectors disposed on a semiconductor substrate, wherein the array of light sources and the array of light detectors are each positioned in spaced relation relative to the semiconductor substrate, and wherein the array of light sources and the array of light detectors are in a staggard configuration, the array of light sources configured to direct light signals at a targeted tissue site in the subject, the array of light detectors configured to capture light signals reflected off the targeted tissue site; and
   a processor coupled with memory and configured to:
      calculate a roundtrip propagation time for each of the light signals; and
      compare the roundtrip propagation time for each of the light signals against one or more corresponding prior roundtrip propagation times to determine an occurrence of a change in a cell structure at the targeted tissue site.

2. The system of claim 1, wherein the processor is further configured to:
   establish a baseline roundtrip propagation time for each light signal, and wherein to compare the roundtrip propagation time includes comparing the roundtrip propagation time for each of the light signals against each of the baseline roundtrip propagation times.

3. The system of claim 2, wherein the implantable biosensor is configured for implantation within the brain of the subject.

4. The system of claim 3, wherein the implantable biosensor includes a penetrating member configured to at least partially penetrate tissue to secure the implantable biosensor adjacent one or more brain cells of the brain.

5. The system of claim 3, wherein the processor is configured to:
   calculate the roundtrip propagation time for each light signal reflected off one or more brain cells of the subject.

6. The system of claim 1, wherein the array of light sources includes a LED array.

7. The system of claim 1, wherein the implantable biosensor includes a communication module configured to transmit data associated with the light signals to the processor.

8. The system of claim 1, wherein the one or more corresponding prior roundtrip propagation times are previously generated by and stored in an external system.

9. The system of claim 1, wherein the semiconductor substrate includes one or more of field-effect transistor devices, bipolar transistors, diodes, capacitors, inductors, resistors, and isolation devices formed in or on an active surface of the semiconductor substrate.

10. The system of claim 1, wherein the implantable biosensor is configured for implantation through an access device through the skull of the subject.

11. The system of claim 10, wherein at least a portion of the access device containing a growth enhancing material is implanted through an aperture of a size of the access device in the bone of the skull.

12. The system of claim 11, wherein the growth enhancing material is bone tissue from the subject.

13. A computer program product for detecting changes in structure of one or more brain cells, comprising:
   a non-transitory computer readable medium encoded with computer-executable code, the code configured to enable the execution of:

calculating roundtrip propagation time of light signals emitted by an implantable biosensor implanted within a subject, the implantable biosensor comprising an array of light sources and an array of light detectors disposed on a semiconductor substrate, wherein the array of light sources and the array of light detectors are each positioned in spaced relation relative to the semiconductor substrate, and wherein the array of light sources and the array of light detectors are in a staggard configuration, the array of light sources configured to direct light signals at a targeted tissue site in the subject, the light detectors configured to capture the light signals reflected off the targeted tissue site; and comparing the roundtrip propagation time for each of the light signals against one or more corresponding prior roundtrip propagation times to determine an occurrence of a change in a cell structure at the targeted tissue site.

14. The computer program product of claim 13, wherein the code is further configured to enable the execution of:

establishing a baseline roundtrip propagation time for each light signal, and wherein comparing the roundtrip propagation time includes comparing the roundtrip propagation time for each of the light signals against each of the baseline roundtrip propagation times.

15. The computer program product of claim 13, wherein the one or more corresponding prior roundtrip propagation times are previously generated by and stored in an external system.

16. The computer program product of claim 13, wherein the implantable biosensor is configured for implantation through an access device through the skull of the subject.

17. The computer program product of claim 16, wherein at least a portion of the access device containing a growth enhancing material is implanted through an aperture of a size of the access device in the bone of the skull.

18. The computer program product of claim 17, wherein the growth enhancing material is bone tissue from the subject.

19. The computer program product of claim 13, wherein the array of light sources includes a LED array.

20. The computer program product of claim 13, wherein the one or more corresponding prior roundtrip propagation times are previously generated by and stored in an external system.

\* \* \* \* \*